United States Patent [19]

Akram et al.

[11] Patent Number: 5,494,489
[45] Date of Patent: Feb. 27, 1996

[54] AQUEOUS COLORANTS FOR KERATIN FIBERS

[75] Inventors: Mustafa Akram, Hamburg; Wolfgang Wolff, Bargteheide, both of Germany

[73] Assignee: Hans Schwarzkopf GmbH, Hamburg, Germany

[21] Appl. No.: 403,528

[22] Filed: Mar. 13, 1995

[30] Foreign Application Priority Data

Mar. 14, 1994 [DE] Germany .......................... 44 08 506.0

[51] Int. Cl.$^6$ ..................................... A61K 7/13
[52] U.S. Cl. .................. 8/408; 8/405; 8/406; 8/409; 8/410; 8/411; 8/435; 8/580; 8/584; 8/586; 8/606
[58] Field of Search ................ 8/404, 405, 406, 8/407, 408, 409, 410, 411, 412, 435, 580, 584, 586, 606

[56] References Cited

U.S. PATENT DOCUMENTS

| 4,209,449 | 6/1990 | Mayhew et al. .......................... 260/403 |
| 4,689,217 | 8/1987 | Restaino et al. ............................. 8/405 |
| 4,690,817 | 9/1987 | Davis et al. ................................. 8/405 |
| 5,135,748 | 8/1992 | Ziegler et al. ........................... 424/401 |
| 5,169,624 | 12/1992 | Ziegler et al. ............................. 424/59 |
| 5,358,667 | 10/1994 | Bergmann ................................ 252/547 |
| 5,420,104 | 5/1995 | Holzner et al. ............................... 512/2 |

FOREIGN PATENT DOCUMENTS 0566049  10/1993  European Pat. Off. .
4234413  4/1994   Germany .

OTHER PUBLICATIONS

Chemical Abstracts, vol. 114 (1991), Nr. 192 230s (p. 424) referring to the International Journal of Cosmetic Science, vol. 12, pp. 209–219, 1990.

*Primary Examiner*—Christine Skane
*Assistant Examiner*—Caroline L. Dusheck
*Attorney, Agent, or Firm*—Beveridge, DeGrandi, Weilacher & Young

[57] ABSTRACT

Improved wet combability of hair is achieved by aqueous colorants for keratin fibers, such as pelts and human hair, based on oxidation dye precursors, which are mixed with a peroxide-containing composition, immediately before use, containing at least one developer substance and at least one coupler substance, and also tris(3-N,N-dimethyl-N-linolenamidopropyl-2-hydroxyammoniumpropyl)phosphoric acid ester-trichloride as a hair care composition. The colored keratin fibers do not show the customary known damage.

9 Claims, No Drawings

AQUEOUS COLORANTS FOR KERATIN FIBERS

INTRODUCTION AND BACKGROUND

The present invention relates to aqueous colorants; for keratin fibers, and more particularly, to compositions for dyeing pelts and human hair. In a further aspect, the present invention relates to a method for coloring pelts and human hair and to the products obtained thereby.

The so-called oxidation dyes, which are formed by oxidative coupling of developer components (such as e.g. p-phenylenediamines, p-aminophenols or p-diaminopyridines) with coupling components (such as e.g. phenols, resorcinols, m-aminophenols, m-phenylenediamines, naphthols or pyrazolones), have particular importance for the coloration of hair. Even when used under marginal conditions (low dyeing temperature and short dyeing period), they afford intense dyeings having very good fastness. The oxidation dyes likewise play an important role in the dyeing of pelts.

Good oxidation dyes must primarily fulfill the following utilization requirements: during oxidative coupling with the particular coupling or developer component, they must afford the desired coloration, which should have a good absorption and leveling ability on the hair or pelts, in adequate intensity. The dyes formed must generally be stable and especially posses good wash-fastness and light-fastness. They must also be perspiration-resistant and heat-stable. In particular, under actual wear conditions they must not be prone to color changes of the original shade. Moreover, they should be toxicologically and dermatologically acceptable.

Aqueous colorants for keratin fibers based on oxidation dye precursors are described by Karlheinz Schrader, "Grundlagen und Rezepturen der Kosmetika" [Foundations and Formulations for Cosmetics], 2nd revised and extended edition, Huethig Buch Verlag, Heidelberg 1989, pages 782 to 815; Hair Coloring, Rev. Prog. Coloration, Vol. 15, 52 ff (1985); J. F. Corbett, The Chemistry of Synthetic Dyes, Vol. 5, edited by Venkataraman, Academic Press, New York and London, 1971.

A requirement for oxidative dyeing, however, is that the oxidation dye precursors must be able to penetrate into the hair. In order to guarantee this, alkalis, preferably ammonia, are added to the hair colorants. As a result of the oxidizing agent, which is not only used for the coupling of the dye precursors, but also destroys the melanin of the hair, and as a result of the alkali, in particular as a result of the ammonia, the hair is appreciably damaged during dyeing. As a result, the hair can be harder to comb. In order to solve this problem, after dyeing the hair is often treated with a shampoo and with a conditioner in two further working steps. This, however, is labor-intensive and does not always lead to satisfactory results.

It is therefore an object of the present invention to find formulations containing specific constituents which are less harsh on the condition of the hair during and after oxidative dyeing.

SUMMARY OF THE INVENTION

In achieving the above and other objects, one feature of the invention resides in aqueous colorants for keratin fibers, such as pelts and human hair, based on oxidation dye precursors, which are mixed immediately before using with a peroxide-containing composition, containing at least one developer substance and at least one coupler substance, and further containing tris(3-N,N-dimethyl-N-linolenamidopropyl-2-hydroxyammoniumpropyl)phosphoric acid ester-trichloride to impart desirable properties to the hair care composition.

More particularly, the above tris(3-N,N-dimethyl-N-linolenamidopropyl- 2-hydroxyammoniumpropyl)phosphoric acid ester-trichloride is preferably present in a concentration of 0.1 to 5% by weight of the total composition.

Typically, the colorants of the invention contain direct-absorbing dyes which are known in the art. Also, the pH of the composition is in the range from approximately 6.0 to 12.5 and preferably in the range from 7.5 to 11.5.

The colorants according to the invention preferably contains one or more developer substances selected from the group consisting of p-phenylenediamine, p-toluylenediamine, 2-hydroxyethyl-1,4-diaminobenzene, p-aminophenol, 3-methyl-4-aminophenol and tetraaminopyrimidine.

With regard to the coupler substance, the invention contain one or more known coupler substances selected from the group consisting of α-naphthol, resorcinol, 4-chlororesorcinol, 2-methylresorcinol, 2-aminophenol, 3-aminophenol, 4-amino-2-hydroxytoluene, 1-methoxy-2-amino-4-(2-hydroxyethyl)aminobenzene, 2-amino-3-hydroxypyridine and 2,6-diaminopyridine.

In a preferred embodiment, the colorant according to the invention is in the form of a coloring cream, the cream base containing one or more of cetyl alcohol, polyacrylic acid, potassium oleate, polymethacrylic acid, decyl oleate, glycerol mono-stearate, polyoxyethylene(10) oleyl ether, polyoxyethylene(30) cetyl/stearyl ether, polyoxyethylene(3) lauryl ether, cetyl/stearyl alcohol, sodium cetyl/stearyl sulphate, polyoxyethylene(40) castor oil, solvents, reducing agents and alkalizing agents such as KOH, NaOH or ammonia.

DETAILED DESCRIPTION OF THE INVENTION

Examples which may be mentioned of developer components which are to be employed are primary aromatic or heteroaromatic amines having another functional group situated in the p-position, such as p-phenylenediamine, p-toluylenediamine, p-aminophenol, 3-methyl-4-aminophenol, 2-hydroxyethyl-1,4-diaminobenzene, tetraaminopyrimidine, 2,5-diaminopyridine and its derivatives, and other compounds of the type mentioned, which additionally carry one or more functional groups, such as OH groups, $HN_2$ groups, NHR groups or NRR groups, R being an optionally substituted alkyl radical having 1 to 4 carbon atoms. Other developer components known to the person skilled in the art can furthermore be used.

Coupler components, such as e.g. α-naphthol, resorcinol, 4-chlororesorcinol, 2-methylresorcinol, m-aminophenol, m-phenylenediamine, m-toluylenediamine, 1,5- or 1,7-dihydroxynaphthalene, 5-amino-2-methylphenol, 6-amino-2-methylphenol or derivatives of the compounds mentioned, can be employed. Other coupler components known to the person skilled in the art can also be employed.

Moreover, the hair colorants can optionally contain customary direct-absorbing dyes, if this is necessary to achieve certain color,shades. The oxidative coupling, i.e. the development of the coloration, can be carried out basically as with other oxidation dyes, even by atmospheric oxygen. Expediently, however, chemical oxidizing agents are employed.

The hair colorants according to the invention are aqueous compositions. Among them are to be understood all compositions which is some way contain water, such as e.g. creams, emulsions, gels or even simple solutions. The composition of the hair colorants is a mixture of the dye components with the additives customary for such cosmetic preparations.

Customary additives in solutions, creams, emulsions or gels are e.g. solvents such as water, lower aliphatic alcohols, for example ethanol, propanol and isopropanol, or glycols, glycerol and glycol ethers such as propylene glycol, furthermore wetting agents or emulsifiers from the classes of anionic, cationic, amphoteric or non-ionic surface-active substances such as fatty alcohol sulphates, alkylsulphonates, alkylbenzenesulphonates, alkyltrimethylammonium salts, alkylbetaines, ethoxylated fatty alcohols, ethoxylated nonylphenols, fatty acid alkanolamides, ethoxylated fatty acid esters, and furthermore thickeners such as higher fatty alcohols, starch, cellulose derivatives, petroleum jelly, liquid paraffin and fatty acids.

The constituents mentioned are used in the amounts customary for such purposes, for example, the wetting agents and emulsifiers in concentrations of approximately 0.5 to 30% by weight, while the thickeners can be contained in the preparations in an amount from approximately 0.2 to 25% by weight.

Depending on the compositions, the hair colorants according to the invention have a weakly acidic, neutral or alkaline reaction. In particular, they have a pH in the alkaline range between 7.5 and 11.5, adjustments preferably being carried out with ammonia. However, organic amines, e.g. monoethanolamine and triethanolamine, or alternatively inorganic bases such as sodium hydroxide and potassium hydroxide, can also be used.

In carrying out processes for the oxidative dyeing of hair, the colorants of this invention, which contain a combination of at least one developer substance known in hair coloration with at least one coupler substance and also tris(3-N,N-dimethyl-N-linolenamidopropyl-2-hydroxyammoniumpropyl)phosphoric acid ester-trichloride and, if desired, additionally direct-absorbing dyes, are mixed with an oxidizing agent shortly before use and this mixture is applied to the hair.

Suitable oxidizing agents for the development of the hair coloration are mainly hydrogen peroxide, for example as a 6% strength aqueous solution, and its addition compounds to urea, melamine or sodium borate as well as mixtures of hydrogen peroxide addition compounds of this type with potassium peroxodisulphate. Hence, any suitable source for hydrogen peroxide can be used which this expression is intended to encompass.

The temperatures used to carry out the process of dyeing in this case vary in the range from 15° to 40° C. After a duration of action of about 30 minutes, the hair colorant is removed from the dyed hair by rinsing. After this the hair can be washed with shampoo. A customary aftertreatment with a conditioning agent is unnecessary.

Hence, another feature of the invention is a system for the dyeing of hair which eliminates a conditioning step as a separate aftertreatment.

The fact that the tris(3-N,N-dimethyl-N-linolenamidopropyl- 2-hydroxyammoniumpropyl)phosphoric acid ester-trichloride, commercial name phospholipid EFA (described un U.S. Pat. No. 4,209,449 incorporated herein by reference) contained in the hair colorant imparts surprisingly advantageous properties to the hair during and after the dyeing process emerges from the following investigations:

The wet-combing forces of several chemically unpretreated strands of hair were determined over a combing distance of 100 mm in the form of a combing force curve (universal test apparatus UTS 2T, for transducer 20 N. max., combing rate 60 mm/minute). Each strand was combed 10 times in this process. For cleaning, the strands were washed exclusively with sodium lauryl sulphate and, after rinsing clear with tap water, left for 10 minutes in 1% strength citric acid and rinsed clear again. Before each combing force measurement, the particular strand lay for at least 15 minutes in tap water at 20° C. for uniform swelling. Before clamping the strand in the measuring apparatus, the individual hairs were completely disentangled by precombing by hand.

The measured strands were then treated as follows:

A. 30 minutes at room temperature in a 1:1 mixture of the colorant cream according to Example 1 and 6% strength $H_2O_2$.

B. 30 minutes at room temperature in a 1:1 mixture of the colorant cream according to Example 1, but without addition of tris(3-N,N-dimethyl-N-linolenamidopropyl-2-hydroxyammoniumpropyl)phosphoric acid ester-trichloride and 6% strength $H_2O_2$.

C. The hair strands treated according to B were treated with a 1% strength solution of tris(3-N,N-dimethyl-N-linolenamidopropyl- 2-hydroxyammoniumpropyl)phosphoric acid ester-trichloride in water for one minute at room temperature. This corresponds to the treatment with a conditioning agent. The investigations have shown:

I. The strands treated according to the invention as in A, show an increase in the wet-combing force by 16.2% compared with untreated strands. This means that the treated hair can readily be combed wet and the damage to the hair is clearly lower in comparison with conventional processes.

II. The strands treated according to the prior art as in B, show an increase in the wet-combing force by 31.1% compared with untreated strands. This means that the treated hair can no longer be readily combed wet and the great damage to the hair is clearly discernible.

III. The strands treated as a comparison as in C, show an increase in the wet-combing force by 36.03% compared with strands treated according to the prior art as in B. This result shows that the hair can no longer readily be combed wet and the greater damage to the hair is clearly discernible. Rinsing with a hair care composition for one minute at room temperature produces no measurable improvement.

The above investigations show that the addition according to the invention of tris(3-N,N-dimethyl-N-linolenamidopropyl- 2-hydroxyammoniumpropyl)phosphoric acid ester-trichloride to the colorant surprisingly succeeds in achieving an improvement in the area of wet-combing behavior during the use of this oxidative hair colorant by 48%. The result of the hair strands treated as in C, shows that the wet-combing behavior cannot be improved by aftertreatment with a 1% strength solution of tris(3-N,N-dimethyl-N-linolenamidopropyl- 2-hydroxyammoniumpropyl)phosphoric acid ester-trichloride, which corresponds to the method of treatment of a conditioning agent.

The following examples are intended to illustrate the subject of the invention in greater detail, but without restricting it hereto.

EXAMPLE 1

The following constituents were processed to give a cream:

| | |
|---|---|
| p-toluylenediamine | 1.85 g |
| m-aminophenol | 0.25 g |
| resorcinol | 0.65 g |
| 1-methoxy-2-amine-4-(2-hydroxyethyl)-aminobenzene sulphate | 0.05 g |
| 1% strength ammonium polyacrylate | 9.00 g |
| 5% strength ammonium polymethacrylate | 2.00 g |
| potassium oleate | 21.50 g |
| polyoxyethylene(10) oleyl ether | 2.00 g |
| titanium dioxide | 0.80 g |
| glycerol monostearate | 2.20 g |
| cetyl alcohol | 13.00 g |
| decyl oleate | 2.30 g |
| cetyl/stearyl alcohol/polyoxyethylene (40) castor oil/sodium cetyl/stearyl sulphate | 1.00 g |
| cetyl/stearyl alcohol/sodium cetyl/stearyl sulphate | 1.50 g |
| polyoxyethylene(30) cetyl/stearyl ether | 1.70 g |
| polyoxyethylene(3) lauryl ether | 1.00 g |
| tris(3-N,N-dimethyl-N-linolenamidopropyl-2-hydroxyammoniumpropyl)phosphoric acid ester-trichloride | 2.00 g |
| 50% strength potassium hydroxide solution | 2.00 g |
| tetrasodium EDTA | 0.50 g |
| sodium dithionite | 0.30 g |
| 25% strength ammonia | 6.00 g |
| perfume | 0.30 g |
| water | to 100 g |

As a hair colorant, 50 g of the above mentioned cream were mixed with 50 g of 6% strength hydrogen peroxide solution shortly before use. The mixture is allowed to act for 30 minutes at room temperature on natural hair which has turned gray. The hair colorant is then rinsed out, and the hair is shampooed and dried. It has taken on a deep medium brown hue. In comparison with hair colored according to the prior art, the wet combability of the colored hair is clearly improved.

EXAMPLE 2

The following constituents were processed to give a cream:

| | |
|---|---|
| p-toluylenediamine | 1.00 g |
| resorcinol | 0.25 g |
| 2-amino-3-hydroxypyridine | 0.10 g |
| 2-methylresorcinol | 0.10 g |
| m-aminophenol | 0.05 g |
| 3-nitro-4-aminophenol | 0.20 g |
| 1% strength ammonium polyacrylate | 9.00 g |
| 5% strength ammonium polymethacrylate | 2.00 g |
| potassium oleate | 21.50 g |
| polyoxyethylene(10) oleyl ether | 2.00 g |
| titanium dioxide | 0.80 g |
| glycerol monostearate | 2.20 g |
| cetyl alcohol | 13.00 g |
| decyl oleate | 2.30 g |
| cetyl/stearyl alcohol/polyoxyethylene (40) castor oil/sodium cetyl/stearyl sulphate | 1.00 g |
| cetyl/stearyl alcohol/sodium cetyl/stearyl sulphate | 1.50 g |
| polyoxyethylene(30) cetyl/stearyl ether | 0.70 g |
| polyoxyethylene(3) lauryl ether | 1.00 g |
| tris(3-N,N-dimethyl-N-linolenamidopropyl-2-hydroxyammoniumpropyl)phosphoric acid ester-trichloride | 2.00 g |
| 50% strength potassium hydroxide solution | 2.00 g |
| tetrasodium EDTA | 0.50 g |
| sodium dithionite | 0.30 g |
| 25% strength ammonia | 6.00 g |
| perfume | 0.30 g |
| water | to 100 g |

As a hair colorant, 50 g of the above mentioned cream were mixed with 50 g of 6% strength hydrogen peroxide solution shortly before use. The mixture is allowed to act for 30 minutes at room temperature on light brown natural hair. The hair colorant is then rinsed out, and the hair is shampooed and dried. It has taken on a deep chestnut hue. The wet combability of the dyed hair in comparison with hair colored according to the prior art is clearly improved.

The invention also features a two package product for sale to the consumer wherein one part of the package is formed of the developer, coupler, the trichlorophosphoric acid ester as well as auxiliary agents, adjuvants and conventional ingredients. The second part of the package is the source of hydrogen peroxide.

We claim:

1. An aqueous dyeing composition for keratin fibers, based on oxidation dye precursors, which is mixed immediately before application with a peroxide-containing composition to form a total composition, comprising at least one developer substance and at least one coupler substance, and 0.1 to 5% by weight of the total composition of tris(3-N,N-dimethyl-N-linolenamidopropyl- 2-hydroxyammoniumpropyl)phosphoric acid ester-trichloride.

2. The composition according to claim 1 further comprising at least one direct-absorbing dye.

3. The composition according to claim 1, which has a pH in the range from approximately 6.0 to 12.5.

4. The composition according to claim 3 wherein the pH is 7.5 to 11.5.

5. The composition according to claim 1 wherein the developer substance is selected from the group consisting of p-phenylenediamine, p-toluylenediamine, 2-hydroxyethyl-1,4-diaminobenzene, p-aminophenol, 3-methyl-aminophenol, tetraaminopyrimidine and mixtures thereof.

6. The composition according to claim 1 wherein the coupler substance is selected from the group consisting of α-naphthol, resorcinol, 4-chlororesorcinol, 2-methylresorcinol, 2-aminophenol, 3-aminophenol, 4-amino-2-hydroxytoluene, 1-methoxy-2-amino-4-(2-hydroxyethyl)aminobenzene, 2-amino-3-hydroxypyridine, 2,6-diaminopyridine and mixtures thereof.

7. A method of applying tris(3-N,N-dimethyl-N-linolenamidopropyl- 2-hydroxyammoniumpropyl)phosphoric acid ester-trichloride to the hair in order to eliminate the need for applying a conditioner to freshly dyed hair comprising treating hair with a dyeing composition according to claim 1.

8. A dyeing cream, comprising a cream base containing at least one of cetyl alcohol, polyacrylic acid, potassium oleate, polymethacrylic acid, decyl oleate, glycerol mono-stearate, polyoxyethylene(10) oleyl ether, polyoxyethylene(30) cetyl/stearyl ether, polyoxyethylene(3) lauryl ether, cetyl/stearyl alcohol, sodium cetyl/stearyl sulphate, polyoxyethylene(40) castor oil, solvents, a reducing agent and an alkalizing agent, said dyeing cream containing at least one developer substance, at least one coupler substance and 0.1 to 5% by weight of tris(3-N,N-dimethyl-N-linolenamidopropyl- 2-hydroxyammoniumpropyl)phosphoric acid ester-trichloride.

9. A two component package product for the dyeing of hair comprising one component comprising a developer, a coupler and 0.1 to 5% by weight of tris(3-N,N-dimethyl-N-linolenamidopropyl-2-hydroxyammoniumpropyl)phosphoric acid ester-trichloride and a second component comprising a source of hydrogen peroxide.

* * * * *